(12) United States Patent
Locke et al.

(10) Patent No.: US 11,708,826 B2
(45) Date of Patent: *Jul. 25, 2023

(54) WOUND TREATMENT APPARATUSES AND METHODS FOR CONTROLLED DELIVERY OF FLUIDS TO A WOUND

(71) Applicant: KCI Licensing, Inc., San Antonio, TX (US)

(72) Inventors: Christopher Brian Locke, Bournemouth (GB); David George Whyte, Wareham (GB)

(73) Assignee: KCI Licensing, Inc., San Antonio, TX (US)

( * ) Notice: Subject to any disclaimer, the term of this patent is extended or adjusted under 35 U.S.C. 154(b) by 469 days.

This patent is subject to a terminal disclaimer.

(21) Appl. No.: 17/089,407

(22) Filed: Nov. 4, 2020

(65) Prior Publication Data

US 2021/0046223 A1    Feb. 18, 2021

Related U.S. Application Data

(63) Continuation of application No. 15/839,076, filed on Dec. 12, 2017, now Pat. No. 10,857,290, which is a
(Continued)

(51) Int. Cl.
*A61M 1/00* (2006.01)
*F04B 43/04* (2006.01)
(Continued)

(52) U.S. Cl.
CPC ............. *F04B 43/04* (2013.01); *A61M 1/72* (2021.05); *A61M 1/80* (2021.05); *A61M 1/92* (2021.05);
(Continued)

(58) Field of Classification Search
CPC .......... A61M 1/72; A61M 1/80; A61M 1/912; A61M 1/92; A61M 1/96; A61M 1/962;
(Continued)

(56) References Cited

U.S. PATENT DOCUMENTS 1,355,846 A    10/1920  Rannells
2,547,758 A     4/1951  Keeling
(Continued)

FOREIGN PATENT DOCUMENTS

AU    550575 B2    3/1986
AU    745271 B2    3/2002
(Continued)

OTHER PUBLICATIONS

First Office Action for corresponding Chinese Application No. 2015102121791, dated Sep. 23, 2016.
(Continued)

*Primary Examiner* — Kai H Weng

(57) ABSTRACT

Pump cassettes, wound-treatment apparatuses and methods. In some embodiments, a pump cassette comprises: a pump body having a pump chamber, an inlet valve in fluid communication with the pump chamber, and an outlet valve in fluid communication with the pump chamber; a diaphragm coupled to the pump body such that the diaphragm is movable to vary a volume in the pump chamber; and an identifier configured to store one or more properties of the pump cassette such that the identifier is readable by an automated reader to determine the one or more properties. In some embodiments, the pump cassette is configured to be removably coupled to a wound-treatment apparatus having an actuator such that the actuator can be activated to move the diaphragm.

20 Claims, 7 Drawing Sheets

Related U.S. Application Data continuation of application No. 14/747,894, filed on Jun. 23, 2015, now Pat. No. 9,872,974, which is a continuation of application No. 13/790,933, filed on Mar. 8, 2013, now Pat. No. 9,089,676, which is a continuation of application No. 13/015,175, filed on Jan. 27, 2011, now Pat. No. 8,394,081.

(60) Provisional application No. 61/299,787, filed on Jan. 29, 2010.

(51) Int. Cl.
| | |
|---|---|
| A61M 5/145 | (2006.01) |
| A61M 5/142 | (2006.01) |
| F04B 43/00 | (2006.01) |
| F04B 45/047 | (2006.01) |
| F04B 43/02 | (2006.01) |
| F04B 45/04 | (2006.01) |
| F04B 35/04 | (2006.01) |

(52) U.S. Cl.
CPC ........ *A61M 1/962* (2021.05); *A61M 5/14224* (2013.01); *A61M 5/14586* (2013.01); *F04B 35/045* (2013.01); *F04B 43/0081* (2013.01); *F04B 43/02* (2013.01); *F04B 45/04* (2013.01); *F04B 45/047* (2013.01); *A61J 2205/00* (2013.01); *A61M 1/912* (2021.05); *A61M 2205/12* (2013.01); *A61M 2205/33* (2013.01); *A61M 2205/3327* (2013.01); *A61M 2205/3337* (2013.01); *A61M 2205/60* (2013.01); *A61M 2205/6054* (2013.01); *A61M 2205/6072* (2013.01)

(58) Field of Classification Search
CPC .......... A61M 2205/12; A61M 2205/33; A61M 2205/3327; A61M 2205/3337; A61M 2205/60; A61M 2205/6054; A61M 2205/6072; A61M 2205/8212; A61M 3/0201; A61M 5/14224; A61M 5/14586; A61J 2205/00; F04B 35/045; F04B 43/0081; F04B 43/02; F04B 43/04; F04B 45/04; F04B 45/047
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,519,792 A | 5/1985 | Dawe | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,431,627 A | 7/1995 | Pastrone et al. | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |

(56) References Cited

U.S. PATENT DOCUMENTS

| | | | |
|---|---|---|---|
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2005/0118048 | A1 | 6/2005 | Traxinger |
| 2007/0107490 | A1 | 5/2007 | Artsyukhovich et al. |
| 2007/0179460 | A1 | 8/2007 | Adahan |
| 2007/0213684 | A1 | 9/2007 | Hickle et al. |
| 2008/0058697 | A1 | 3/2008 | Kamen et al. |
| 2008/0082077 | A1 | 4/2008 | Williams |
| 2009/0036846 | A1 | 2/2009 | Dacquay et al. |
| 2009/0127325 | A1 | 5/2009 | Macurek et al. |
| 2009/0264837 | A1 | 10/2009 | Adahan |
| 2009/0312725 | A1 | 12/2009 | Braga |
| 2014/0163491 | A1 | 6/2014 | Schuessler et al. |
| 2015/0080788 | A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 9528190 A1 | 10/1995 |
| WO | 96/05873 A1 | 2/1996 |
| WO | 97/18007 A1 | 5/1997 |
| WO | 9806446 A2 | 2/1998 |
| WO | 99/13793 A1 | 3/1999 |
| WO | 2009004370 A1 | 1/2009 |

OTHER PUBLICATIONS

Extended European Search Report for corresponding Application No. 117376442, dated Dec. 21, 2017.

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Septembers, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by

(56) References Cited

OTHER PUBLICATIONS

V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Dbstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

D.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

WOUND TREATMENT APPARATUSES AND METHODS FOR CONTROLLED DELIVERY OF FLUIDS TO A WOUND

CROSS-REFERENCE TO RELATED APPLICATIONS

This application is a continuation of U.S. patent application Ser. No. 15/839,076, filed Dec. 12, 2017, which is a continuation of U.S. patent application Ser. No. 14/747,894, filed Jun. 23, 2015, now U.S. Pat. No. 9,872,974, which is a continuation of U.S. patent application Ser. No. 13/790,933, filed Mar. 8, 2013, now U.S. Pat. No. 9,089,676, which is a continuation of U.S. patent application Ser. No. 13/015,175, filed Jan. 27, 2011, now U.S. Pat. No. 8,394,081, which claims priority to U.S. Provisional Patent Application No. 61/299,787, filed Jan. 29, 2010, which is incorporated herein in its entirety.

BACKGROUND

1. Field of the Invention

The present disclosure relates generally to healing of wounds and wound-treatment therapies. More particularly, but not by way of limitation, the present disclosure relates to fluid-instillation and negative-pressure wound therapies.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device). The wound insert typically contains cells or pores that are capable of distributing reduced pressure to the tissue and channeling fluids that are drawn from the tissue. The wound insert can be incorporated into a wound dressing having other components that facilitate treatment, such as, for example, a drape (e.g., adhesive surgical drape).

SUMMARY

The present disclosure includes embodiments of pump cassettes, wound-treatment apparatuses, and methods.

Some embodiments of the present pump cassette for use with a wound treatment apparatus, comprise: a pump body having a pump chamber, an inlet valve in fluid communication with the pump chamber, and an outlet valve in fluid communication with the pump chamber; a diaphragm coupled to the pump body such that the diaphragm is movable to vary a volume in the pump chamber; and an identifier configured to store one or more properties of the pump cassette such that the identifier is readable by an automated reader to determine the one or more properties; where the pump cassette is configured to be removably coupled to a wound-treatment apparatus having an actuator such that the actuator can be activated to move the diaphragm. In some embodiments, the identifier comprises a radio-frequency identification (RFID) tag. In some embodiments, the identifier comprises a barcode. In some embodiments, the identifier comprises a magnetic stripe. In some embodiments, the one or more properties include one or more of: the diameter of the diaphragm, the area of the diaphragm, the stroke of the diaphragm, the change in volume in the pump chamber caused by a stroke of the diaphragm, and a code indicative of one or more properties of the pump cassette. In some embodiments, the inlet valve and outlet valve each comprises a ball valve. In some embodiments, the inlet valve and outlet valve each comprises a duckbill valve. In some embodiments, the inlet valve and outlet valve each comprises an umbrella valve.

Some embodiments further comprise: a conduit having a first end coupled to the inlet valve of the pump body, and a second end configured to be coupled to a fluid container. Some embodiments, further comprise: a fluid container coupled to the second end of the conduit such that the fluid container is in fluid communication with the inlet valve of the pump body; and a fluid disposed in the fluid container. In some embodiments, the one or more properties include the identity of the fluid disposed in the fluid container. Some embodiments further comprise: a support device coupled to the pump body and including a receptacle configured to receive a fluid container.

Some embodiments of the present wound-treatment apparatuses comprise: a housing configured to be coupled to a pump cassette; a vacuum source coupled to the housing and configured to be coupled to a wound dressing such that the vacuum source can be activated to apply negative pressure to a wound through the wound dressing; an actuator coupled to the housing; and an automated reader configured to read an identifier of a pump cassette coupled to the housing to determine one or more properties of the pump cassette; where the wound-treatment apparatus is configured such that if an embodiment of the present pump cassettes is coupled to the housing, the automated reader can read the identifier of the pump cassette to determine one or more properties of the pump cassette, and the actuator can be activated to move the diaphragm.

In some embodiments, the housing is configured to be coupled to one or more of the present pump cassettes, and the wound-treatment apparatus comprises: a plurality of actuators coupled to the housing; where the wound-treatment apparatus is configured such that if one or more pump cassettes, each having at least one pump chamber and at least one diaphragm configured to be movable to vary a volume in a pump chamber, are coupled to the housing, the plurality of actuators can be activated to move the diaphragms. Some embodiments further comprise: a controller coupled to the actuators and configured to activate the actuators. In some embodiments, the controller is configured to activate the actuators simultaneously. In some embodiments, the controller is configured to activate the actuators sequentially. Some embodiments further comprise: a plurality of automated readers each configured to read an identifier of the one or more pump cassettes to determine one or more properties of the one or more pump cassettes; where the wound-treatment apparatus is configured such that if one or more pump cassettes each having an identifier are coupled to the housing, the one or more automated readers can read the identifiers to determine the one or more properties. Some embodiments further comprise: one or more pump cassettes of claim 1 each having a plurality of pump chambers and a plurality of diaphragms configured to be movable to vary a volume in each of the plurality of pump chambers. In some embodiments, at least one of the plurality of diaphragms is a different size than at least one other of the plurality of diaphragms. In some embodiments, the plurality of pump cassettes are coupled to the housing. Some embodiments further comprise: a fluid container. In some embodiments, the input valve of each of the plurality of pump cassettes is coupled to the fluid container. Some embodiments further comprise: a vacuum source coupled to the housing and configured to be coupled to a wound dressing such that the vacuum source can be activated to apply negative pressure to a wound through the wound dressing.

Some embodiments of the present wound-treatment apparatuses, comprise: housing configured to be coupled to a pump cassette comprising: a pump body having a pump chamber, inlet valve in fluid communication with the pump chamber, and an outlet valve in fluid communication with the pump chamber; and a diaphragm coupled to the pump body such that the diaphragm is movable to vary a volume in the pump chamber; a vacuum source coupled to the housing and configured to be coupled to a wound dressing such that the vacuum source can be activated to apply negative pressure to a wound through the wound dressing; and an actuator coupled to the housing; where the wound-treatment apparatus is configured such that if the pump cassette is coupled to the housing the actuator can be activated to move the diaphragm.

Some embodiments of the present wound-treatment apparatuses comprise: a vacuum source configured to be coupled to a wound dressing such that the vacuum source can be activated to apply negative pressure to a wound through the wound dressing; an actuator for moving a diaphragm of a pump cassette coupled to the housing; and an automated reader configured to read an identifier of a pump cassette coupled to the housing to determine one or more properties of the pump cassette. Some embodiments further comprise: a plurality of actuators, each for moving a diaphragm of a pump cassette coupled to the housing. In some embodiments, the apparatus is configured to be coupled to a plurality of pump cassettes. In some embodiments, the apparatus is configured to actuate the actuators simultaneously. In some embodiments, the apparatus is configured to actuate the actuators sequentially. Some embodiments further comprise: a plurality of automated readers, each reader configured to read an identifier of a pump cassette coupled to the housing. In some embodiments, the apparatus is coupled to one of the present pump cassettes. In some embodiments, the apparatus is coupled to a plurality of the present pump cassettes.

Some embodiments of the present methods comprise: coupling a wound dressing to a wound-treatment apparatus that comprises; a housing configured to be coupled to a pump cassette comprising: a pump body having a pump chamber, inlet valve in fluid communication with the pump chamber, and an outlet valve in fluid communication with the pump chamber; and a diaphragm coupled to the pump body such that the diaphragm is movable to vary a volume in the pump chamber; a vacuum source coupled to the housing and configured to be activated to apply negative pressure to a wound through the wound dressing; and an actuator coupled to the housing. Some embodiments further comprise: coupling a pump cassette to the housing of the wound treatment apparatus such that actuator can be activated to move the diaphragm and such that the outlet valve is in fluid communication with the wound dressing. Some embodiments further comprise: activating the actuator to move the diaphragm such that fluid is delivered to the wound dressing. In some embodiments, coupling a pump cassette is performed prior to coupling a wound dressing. Some embodiments further comprise: activating the vacuum source such that negative pressure is applied to the wound dressing.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises a wound insert and a drape, the wound dressing includes the specified elements but is not limited to having only those elements. For example, such a wound dressing could also include a connection pad configured to be coupled to a wound-treatment apparatus.

Further, a device or structure that is configured in a certain way is configured in at least that way, but it can also be configured in other ways than those specifically described.

Figure 1:
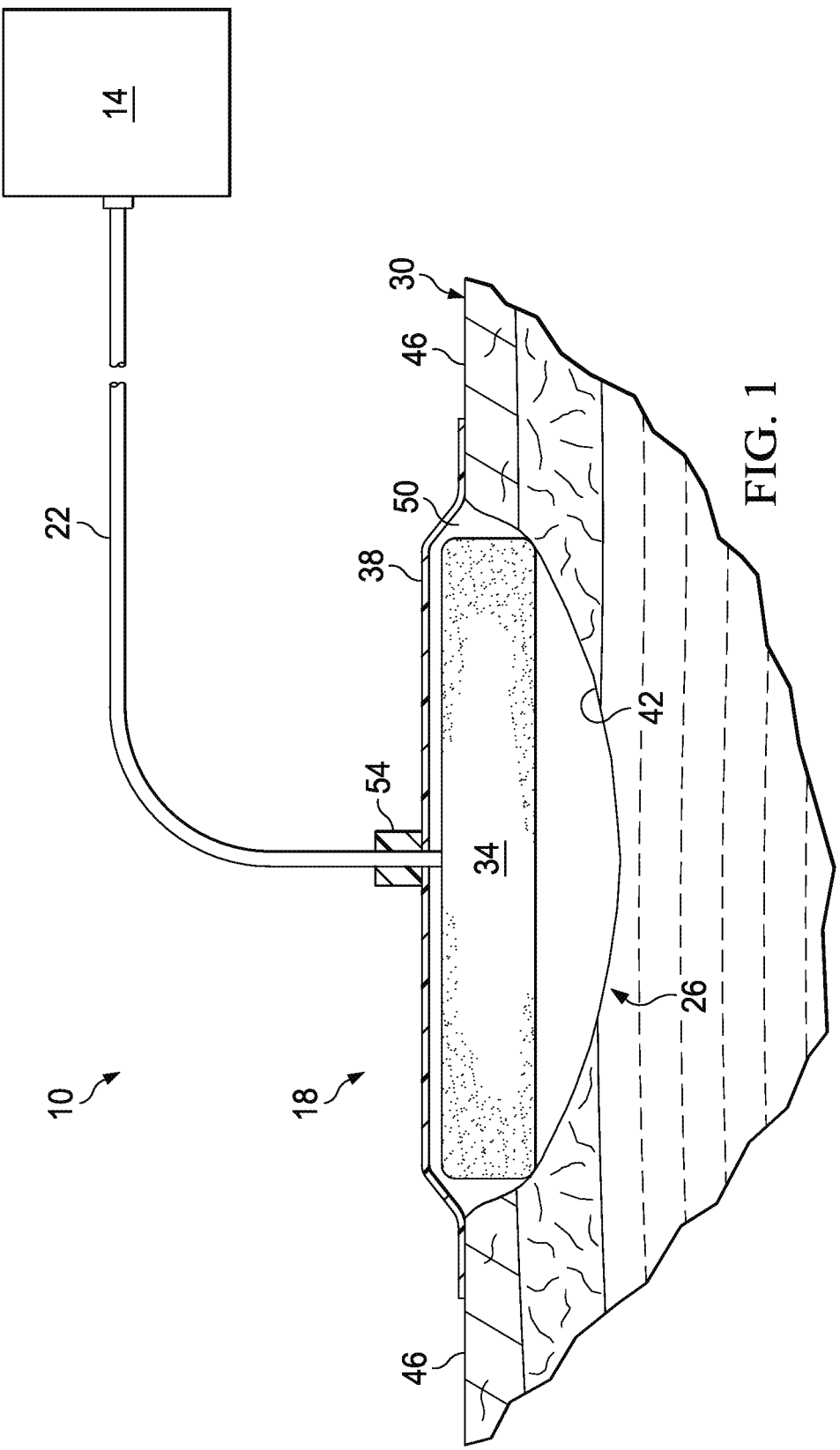
FIG. 1 depicts a side view of one embodiment of the present wound dressings having one of the present wound inserts and coupled to a wound site and to a wound treatment apparatus.

Referring now to the drawings, and more particularly to FIG. 1, shown therein is an embodiment of one of the present wound treatment system 10. In the embodiment shown, apparatus 10 comprises a wound-treatment apparatus 14, and a wound dressing 18 coupled to apparatus 14 by a conduit 22. As shown, dressing 18 is configured to be coupled to (and is shown coupled to) a wound 26 of a patient 30. More particularly, in the embodiment shown, dressing 18 comprises a wound insert 34 and a drape 38. As shown, wound insert 34 is configured to be positioned (and is shown positioned) on wound 26 (e.g., on or adjacent to wound surface 42), and/or drape 38 is configured to be coupled to (and is shown coupled to) skin 46 of the patient adjacent to wound 26 such that drape 38 covers wound insert 34 and wound 26, and forms a space 50 between drape 38 and wound 26 (e.g., wound surface 42).

Apparatus 14 can comprise, for example, a vacuum source configured to be actuatable (and/or actuated) to apply negative pressure (e.g., via conduit 22) to wound dressing 18, a fluid (e.g., liquid or foamed fluid) source configured to be actuatable (and/or actuated) to deliver (e.g., via conduit 22) a fluid (e.g., an instillation fluid such as a medicinal liquid, antibacterial liquid, irrigation liquid, foamed fluid, and/or the like) to wound dressing 18. System 10 can be implemented and/or actuated and/or coupled to patient 30 in any of various configurations and/or methods similar to those described in the prior art. For example, various wound therapy systems and components are commercially available through and/or from KCI USA, Inc. of San Antonio, Tex., U.S.A., and/or its subsidiary and related companies (collectively, "KCI").

Conduit 22 can comprise a single lumen conduit (e.g., switched between a vacuum source and/or a fluid source and apparatus 14), or can comprise multiple single-lumen conduits or a multi-lumen conduit such that, for example, fluid can be delivered and/or negative pressure can be applied to wound dressing 18 individually and/or simultaneously. Additionally, conduit 22 can comprise, for example, multiple lumens (e.g., as in a single conduit with a central lumen for application of negative pressure and/or fluid delivery and one or more peripheral lumens adjacent to or around the central lumen, such that the peripheral lumens can be coupled to a pressure sensor to sense a pressure or negative pressure between drape 38 and surface 42 (e.g. in space 50)). In the embodiment shown, system 10 further comprises a wound dressing connection pad 54 configured to be coupled (and is shown coupled) to conduit 22. One example of a suitable connection pad 54 is the "V.A.C. T.R.A.C.® Pad," commercially available from KCI. Another example of a connection pad 54 is disclosed in U.S. patent application Ser. No. 11/702,822, published as Pub. No. US 2007/0219512 A1. One example of a suitable drape 38 includes the "V.A.C.® Drape" commercially available from KCI.

Figure 2:
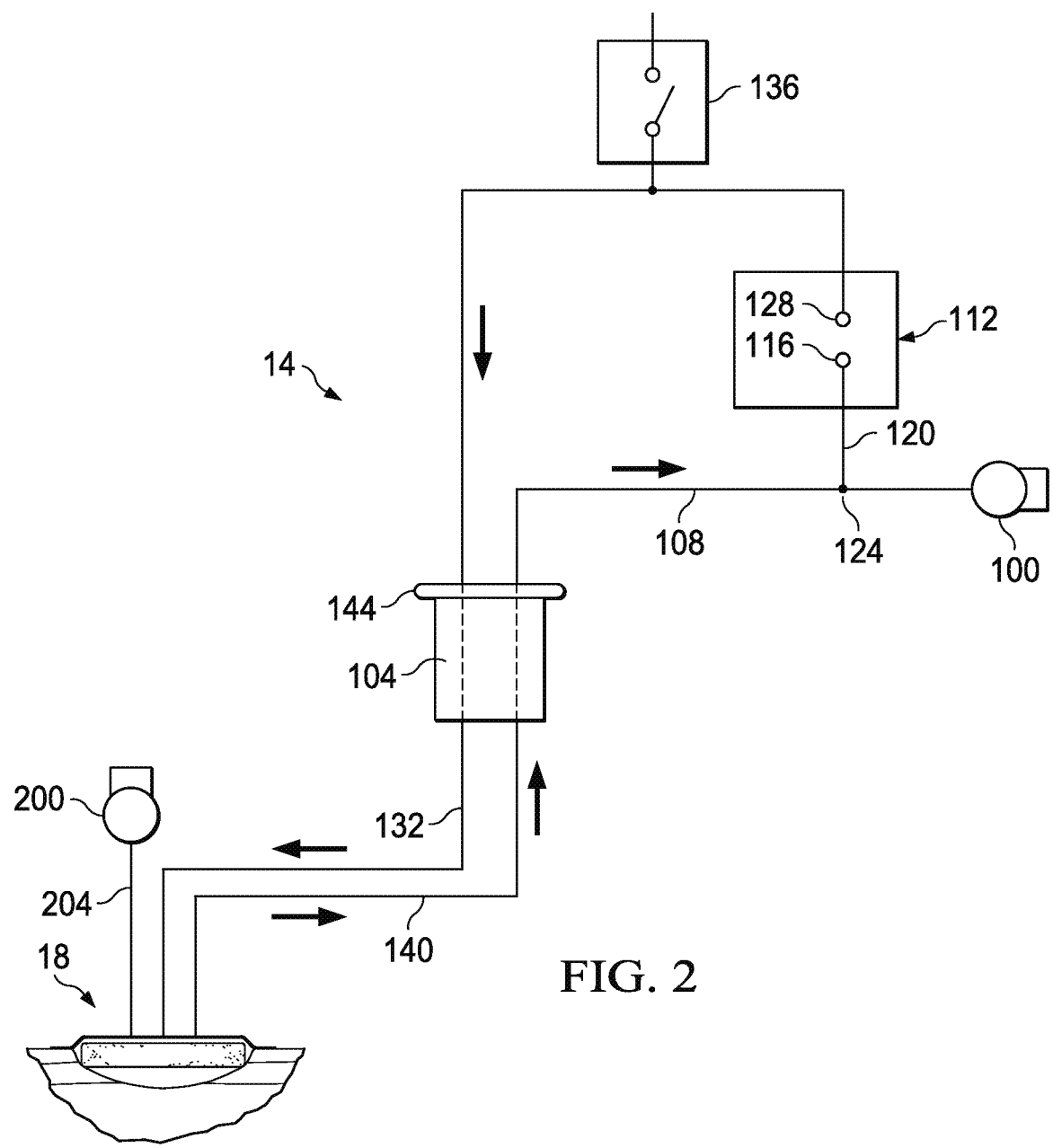
FIG. 2 depicts a schematic block diagram of one embodiment of a wound treatment apparatus that can comprise and/or be coupled to and/or be used with the present wound dressings and/or wound inserts.

Some embodiments of the present wound-treatment apparatuses and methods may be better understood with reference to FIG. 2. FIG. 2 depicts the schematic block diagram of one embodiment of system 10. In the embodiment shown, wound dressing 18 is coupled to apparatus 14, and apparatus 14 comprises a vacuum source 100 (e.g., a vacuum pump and/or the like) coupled to a canister 104 (e.g., configured to receive exudate and or the like from wound dressing 18) by way of a conduit 108. In the embodiment shown, apparatus 14 further comprises: a pressure sensor 112 having a first pressure transducer 116 coupled to conduit 108 by way of conduit 120 and/or tee-fitting 124, and a second pressure transducer 128 coupled to canister 104 and/or wound dressing 18 by way of conduit 132. Pressure sensor 112 is configured to sense the negative pressure in wound dressing 18 and/or any of the various conduits coupled to wound dressing 18, pressure sensor 112, and/or vacuum source 100.

In the embodiment shown, apparatus 14 further comprises a pressure release valve 136 coupled to conduit 132. Further, in the embodiment shown, canister 104 and vacuum source 100 are coupled to wound dressing 18 by way of a conduit 140. More particularly, conduit 140 couples canister 104 to wound dressing 18. In the embodiment shown, canister 104 comprises a filter 144 at or near an outlet of canister 104 to prevent liquid or solid particles from entering conduit 108. Filter 144 can comprise, for example, a bacterial filter that is hydrophobic and/or lipophilic such that aqueous and/or oily liquids will bead on the surface of the filter. Apparatus 14 can be configured such that during operation of vacuum source 100 will provide sufficient airflow through a filter 144 that the pressure drop across filter 144 is not substantial (e.g., such that the pressure drop will not substantially interfere with the application of negative pressure to wound dressing 18 from vacuum source 100).

In various embodiments, such as the one shown in FIG. 2, apparatus 14 can be configured such that as soon as liquid in the canister reaches a level where filter 144 is occluded, a much-increased negative (or subatmospheric) pressure occurs in conduit 108 and is sensed by transducer 116. Transducer 116 can be connected to circuitry that interprets such a pressure change as a filled canister and signals this by means of a message on an LCD and/or buzzer that canister 104 requires emptying and/or replacement, and/or that automatically shuts off or disables vacuum source 100.

Apparatus 14 can also be configured to apply intermittent negative (or subatmospheric) pressure to the wound site, and/or such that pressure relief valve 136 enables pressure at the wound site to be brought to atmospheric pressure rapidly. Thus, if apparatus 14 is programmed, for example, to relieve pressure at ten-minute intervals, at these intervals pressure relief valve 136 can open for a specified period, allow the pressure to equalize at the wound site, and then close to restore the negative pressure. It will be appreciated that when constant negative pressure is being applied to the wound site, valve 136 remains closed to prevent leakage to or from the atmosphere. In this state, it is possible to maintain negative pressure at the wound site without running and/or operating pump 100 continuously, but only from time to time or periodically, to maintain a desired level of negative pressure (i.e. a desired pressure below atmospheric pressure), which is sensed by transducer 116. This saves power and enables the appliance to operate for long periods on its battery power supply.

In the embodiment shown, apparatus 14 further comprises a fluid source 200 coupled to wound dressing 18 by way of a conduit 204 such that such that fluid source 200 is actuatable to deliver a fluid to wound dressing 18 (e.g., to the wound through the wound dressing). Fluid source 200 can be any suitable mechanism capable of delivering fluid, such as, for example, a syringe, a fluid pump, and/or the like.

Figure 3:
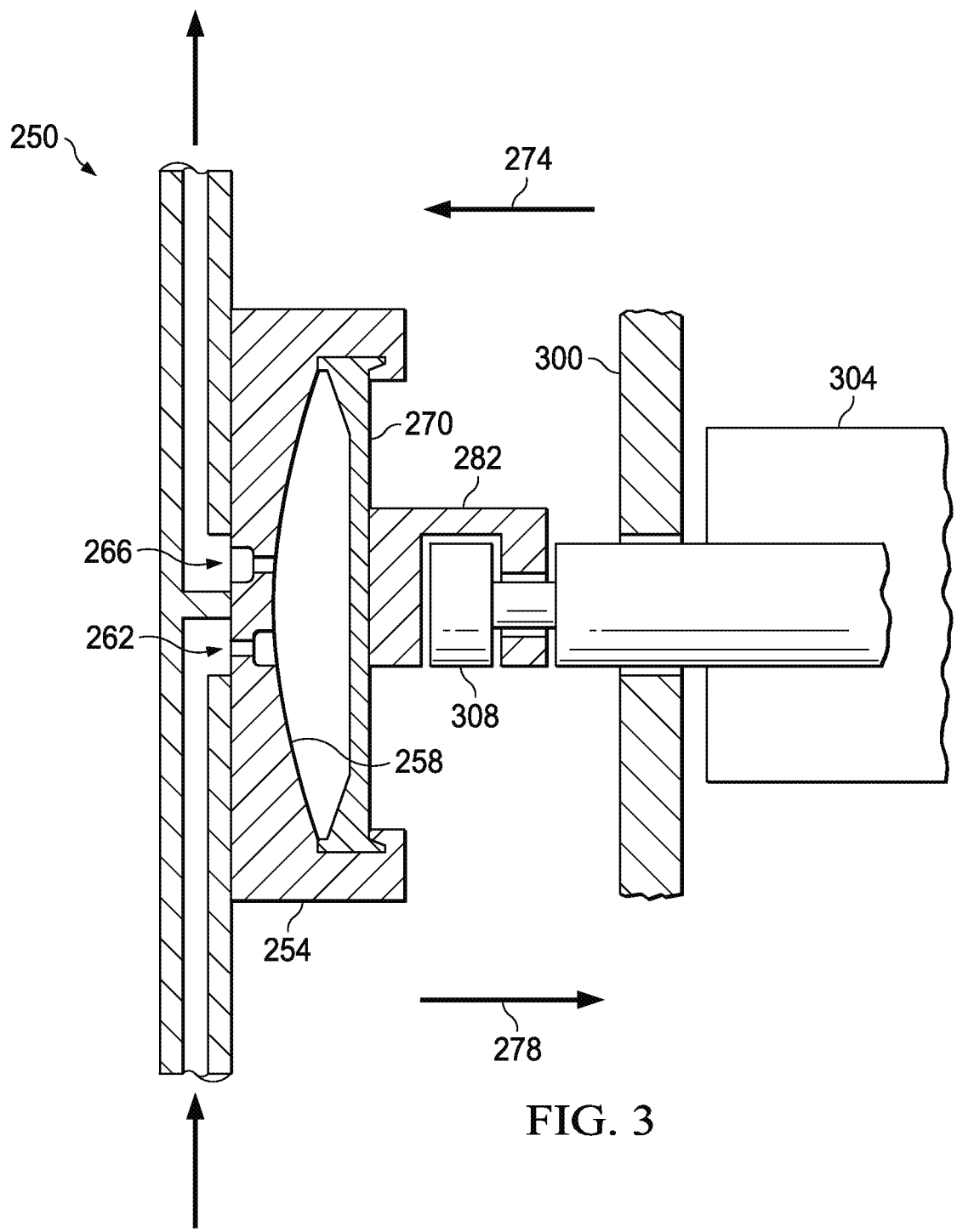
FIG. 3 depicts an enlarged cross-sectional view of a portion of one embodiment of the present pump cassettes.
Figure 6:
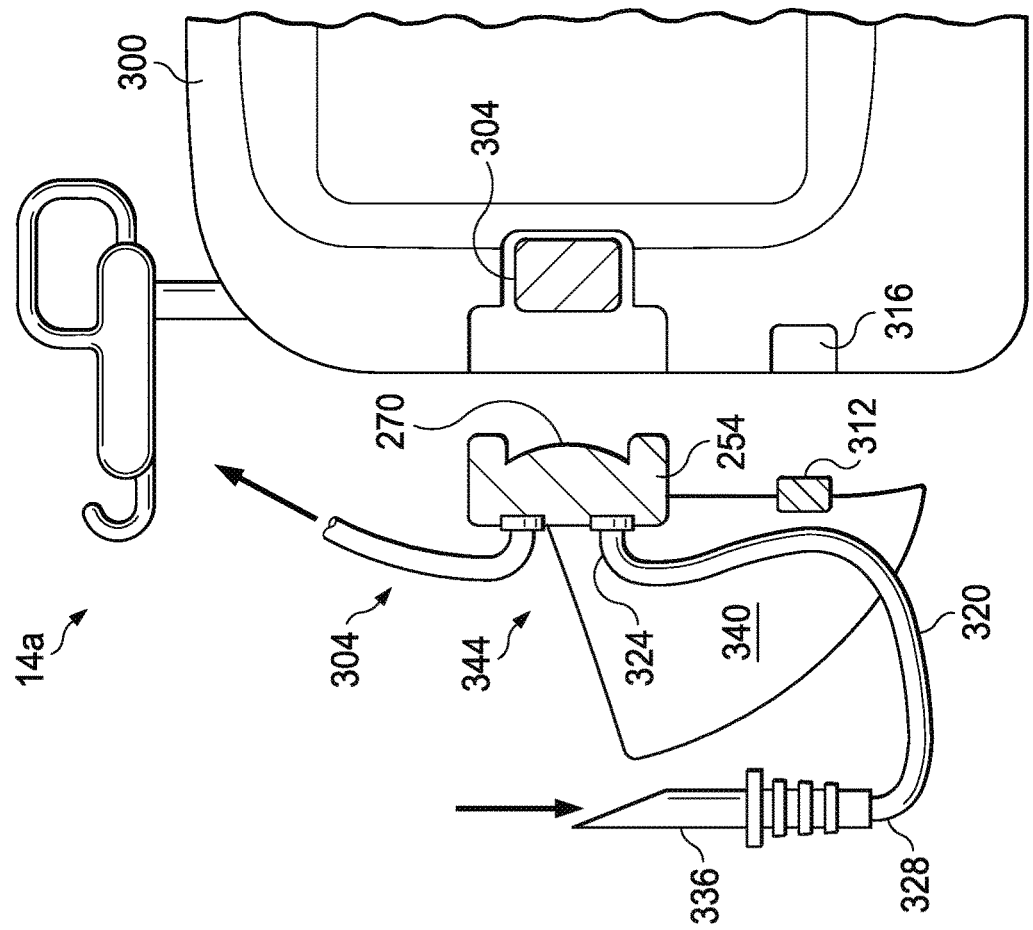
FIGS. 5 and 6 depicts a side view of the apparatus of FIG. 4.
Figure 5:
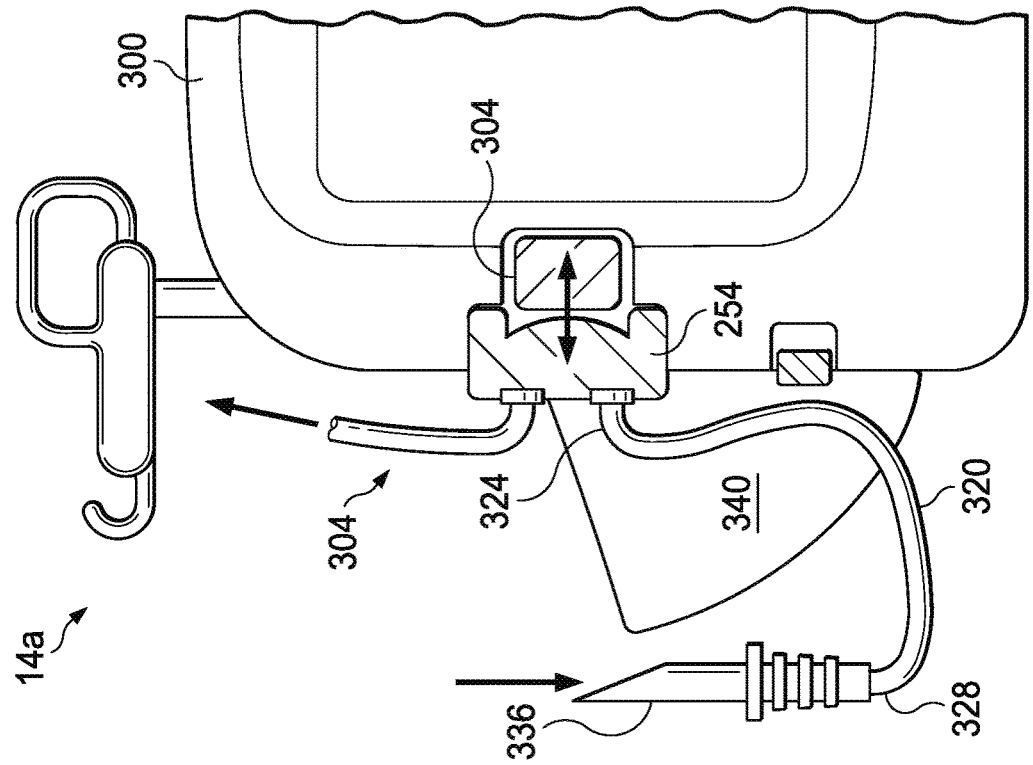

FIG. 3 depicts an enlarged cross-sectional view of a portion of one embodiment 250 of the present pump cassettes that is suitable for use in some embodiments of fluid source 200. In the embodiment shown, pump cassette 250 comprises: a pump body 254 having a pump chamber 258, an inlet valve 262 in fluid communication with pump chamber 258, and an outlet valve 266 in fluid communication with pump chamber 258. In the embodiment shown, pump cassette 250 further comprises a diaphragm 270 coupled to pump body 254 such that diaphragm 270 is movable to vary a volume in pump chamber 258 (e.g., the volume between pump body 254 and diaphragm 270). In the embodiment shown, and as depicted in FIGS. 5 and 6, pump cassette 250 is configured to be removably coupled to a wound-treatment apparatus having an actuator such that the actuator (e.g., 304) can be activated to move diaphragm 270 (e.g., relative to pump body 254) such as, for example, to pump fluid through pump cassette 250 (e.g., from inlet valve 262 to outlet valve 266). In the embodiment shown, inlet valve 262 and outlet valve 266 each comprise a one-way valve, such as, for example, ball valves, duckbill valves, umbrella valves, etc. As such, when diaphragm 270 is moved (e.g., by actuator 304) in direction 274, inlet valve 262 closes, and outlet valve 266 opens, such that fluid is forced out of pump chamber 258 as the volume between diaphragm 270 and pump body 254 decreases. Similarly, when diaphragm 270 is moved (e.g., by actuator 304) in direction 278, outlet valve 266 closes, and inlet valve 262 opens, such that fluid is drawn into pump chamber 258 as the volume between diaphragm 270 and pump body 254 increases. In the embodiment shown, diaphragm 270 (e.g., the center of diaphragm 270) is removably coupled to a distal end 308 of actuator 304 by a slotted connector 282 configured to couple diaphragm 270 and end 308 of actuator 304 such that end 308 can push and pull diaphragm 270 (e.g., can move diaphragm in two substantially opposite directions). In other embodiments, any suitable mechanical coupling structure or mechanism can be used, such as, for example, a pin or cotter pin, a threads on end 308 and corresponding threads on connector 282, magnets and/or magnetic materials, and/or the like.

In some embodiments, pumping cavity 258 is shaped such that when diaphragm 270 (e.g., end 308) is fully extended (diaphragm 270 and end 308 are as close as possible to valves 262 and 266), the circumference about exit valve 266 is sealed by the diaphragm, such that if negative pressure is applied to the wound dressing, negative pressure is substantially prevented (e.g., by diaphragm 270 and inlet valve 266) from being transferred through the pump chamber (which might otherwise draw fluids from the fluid container to the wound and/or collection canister).

Figure 4:
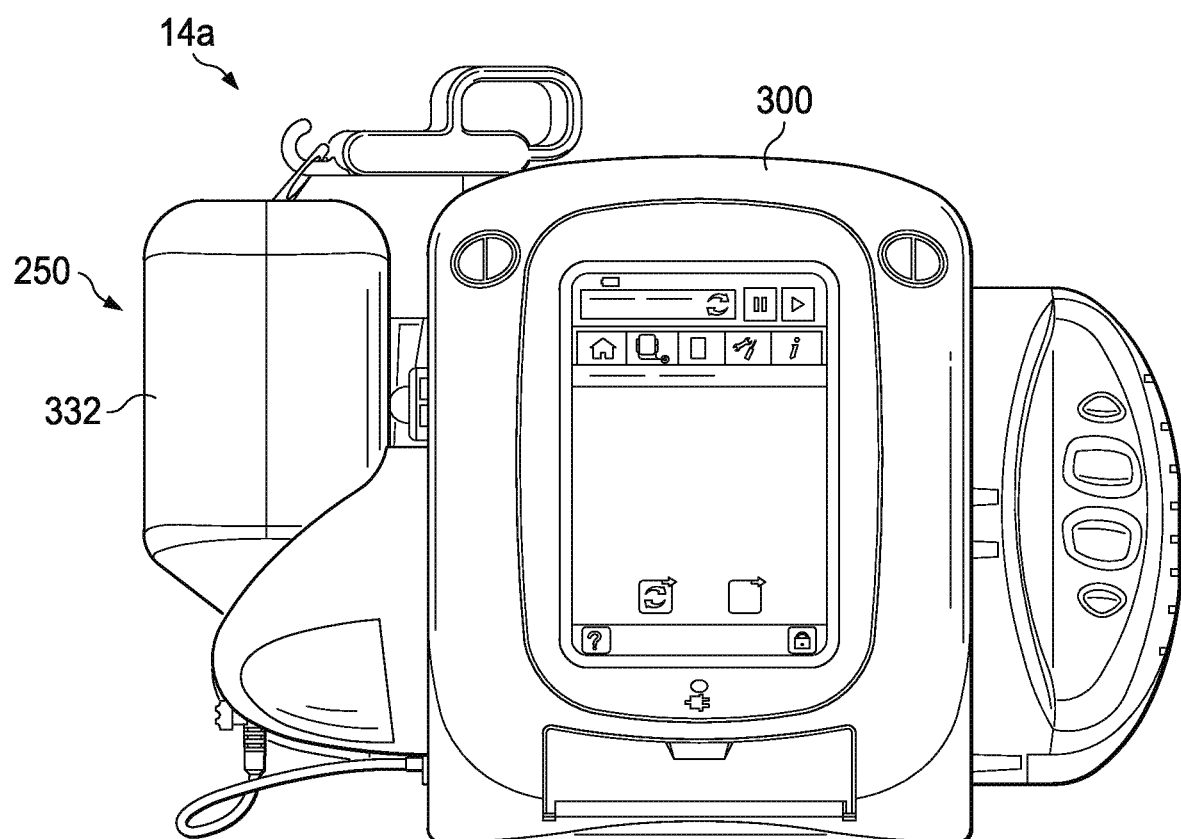
FIG. 4 depicts a perspective view of one embodiment of the present wound-treatment apparatuses.

FIGS. 4-6 depict one embodiment of the present wound-treatment apparatuses 14a that may be similar to the apparatus 14 of FIG. 2. More particularly, FIG. 3 depicts a view of an overall apparatus 14a; FIGS. 4 and 5 depict partial view of apparatus 14a and illustrate the removability of one embodiment of the present pump cassettes; and FIG. 6 depicts an enlarged view of one embodiment of the present pump cassettes. Apparatus 14a comprises: a housing 300 configured to be coupled to a pump cassette 250 (e.g., such that pump body 254 is in substantially fixed relationship to housing 300). In the embodiment shown, apparatus 14a further comprises an actuator 304 coupled to housing 300. As described above, pump cassette 250 includes a pump chamber 258 and a membrane 270 configured to be movable to vary the volume of the pump chamber (e.g., to pump fluid through the pump cassette). Actuator 304 is configured such that if pump cassette 250 is coupled to housing 300 (as shown in FIG. 4), actuator 304 can be activated to move the diaphragm of the pump cassette (e.g., to pump fluid through the pump cassette). In the embodiment shown, actuator 304 comprises a solenoid with a linear stroke that can oscillate end 308 and diaphragm 270 to sequentially decrease and increase a volume in the pump chamber (between diaphragm 270 and pump body 254) to pump fluid through the pump cassette. In other embodiments, actuator 304 can comprise any suitable actuator or actuating mechanism, such as, for example, a cam mechanism, a rack and pinion mechanism, a gearbox, an eccentric arm from a motor, and/or any other suitable actuator that permits pump cassette 250 and/or apparatus 14a to function as described in the present disclosure.

In the embodiment shown, pump cassette 250 also comprises an identifier 312 configured to store one or more properties of the pump cassette such that the identifier is readable by an automated reader to determine the one or more properties. In the embodiment shown, apparatus 14a further comprises an automated reader 316 configured to read identifier 312 of the pump cassette to determine the one or more properties (stored on or readable from the identifier). Apparatus 14a can also be configured such that if pump cassette 250 is coupled to housing 300 (as shown in FIG. 4), automated reader 316 can read identifier 312 of pump cassette 250 to determine the one or more properties (stored on or readable from identifier 312). Identifier 312 can comprise any suitable device or structure, such as, for example, a radio-frequency identification (RFID) tag, barcode, a magnetic stripe (e.g., as is commonly used on credit cards and the like), and/or any other suitable identifier that can be read by automated reader 316. In some embodiments, identifier comprises flash memory, a processor, and/or a wireless transceiver. Reader 316 can comprise any suitable device or structure, such as, for example, an RFID reader (for RFID tags), a barcode reader (for barcodes), a magnetic-stripe reader (for magnetic stripes), and so on. In some embodiments, the one or more properties (stored on or readable from identifier 312) can include one or more of: the diameter of diaphragm 270, the area of diaphragm 270, the stroke of diaphragm 270 (linear distance through which the center of diaphragm 270 can be actuated), the change in volume in pump chamber 258 (e.g., between diaphragm 270 and pump body 254) caused by a stroke of diaphragm 270, and a code indicative of one or more properties of pump cassette 250. In some such embodiments, apparatus 300 can comprise a controller and/or memory (not shown) that is coupled to reader 316 and programmed to recognize a code stored on identifier 312 and activate actuator 308 in a predetermined or preprogrammed fashion corresponding to the one or more properties of pump cassette 250 identified by a code obtained from identifier 312 with reader 316. In some embodiments, the pump cassette does not comprise an identifier that is readable by an automated reader, and is instead labeled with one or more of its properties; and, in such embodiments, apparatus 14a can comprise one or more switches and/or a touch-screen to permit a user to manually select one or more apparatus settings that correspond to a particular pump cassette (e.g., how to alter the frequency and stroke of the actuator to best drive the diaphragm, and/or which range of user selectable options should be displayed on the user interface).

In some embodiments, pump cassette 250 comprises a conduit 320 having a first end 324 coupled to inlet valve 262 of pump body 254, and a second end 328 configured to be coupled to a fluid container 332 (e.g., via spike 336). In some embodiments, pump cassette 250 comprises: fluid container 332 coupled to second end 328 of conduit 320

(e.g., via spike 336) such that fluid container 332 is in fluid communication with inlet valve 262 of pump body 254; and a fluid disposed in fluid container 332. The fluid in fluid container 332 can comprise any suitable fluid or component, such as, for example, saline, debridement agent, and/or antibiotic. In embodiments in which pump cassette 250 comprises fluid container 332, the one or more properties (stored on or readable from identifier 312), can include the identity of the fluid disposed in fluid container 332. In some embodiments, pump cassette 250 also comprises a support device 340 (e.g., coupled to pump body 254) that includes a receptacle 344 configured to receive a fluid container (e.g., fluid container 332).

In some embodiments, the pump cassette is disposable, such that it can be replaced periodically by a user, and/or can be included in the present kits that can comprise one or pump cassettes, a wound dressing (e.g., 18), a fluid container (e.g., 332), a fluid disposed in the fluid container, and/or a conduit for coupling the wound dressing to the pump cassette and/or a wound treatment apparatus (e.g., 14, 14a). Disposable pump cassettes can increase the service life of the apparatus because the high-wear components of the pump (e.g., the diaphragm, etc.) are in the disposable pump cassette that is easily replaceable. Additionally, disposable pump cassettes can improve cleanliness and reduce risks of infections and/or cross-contamination because the fluids can be retained in the pump cassette without transfer to the remainder of the apparatus.

In some embodiments, apparatus 14a comprises a vacuum source (e.g., 100) coupled to housing 300 and configured to be coupled to a wound dressing (e.g., 18) such that the vacuum source can be activated to apply negative pressure to a wound (e.g., 26) through the wound dressing.

Figure 7:
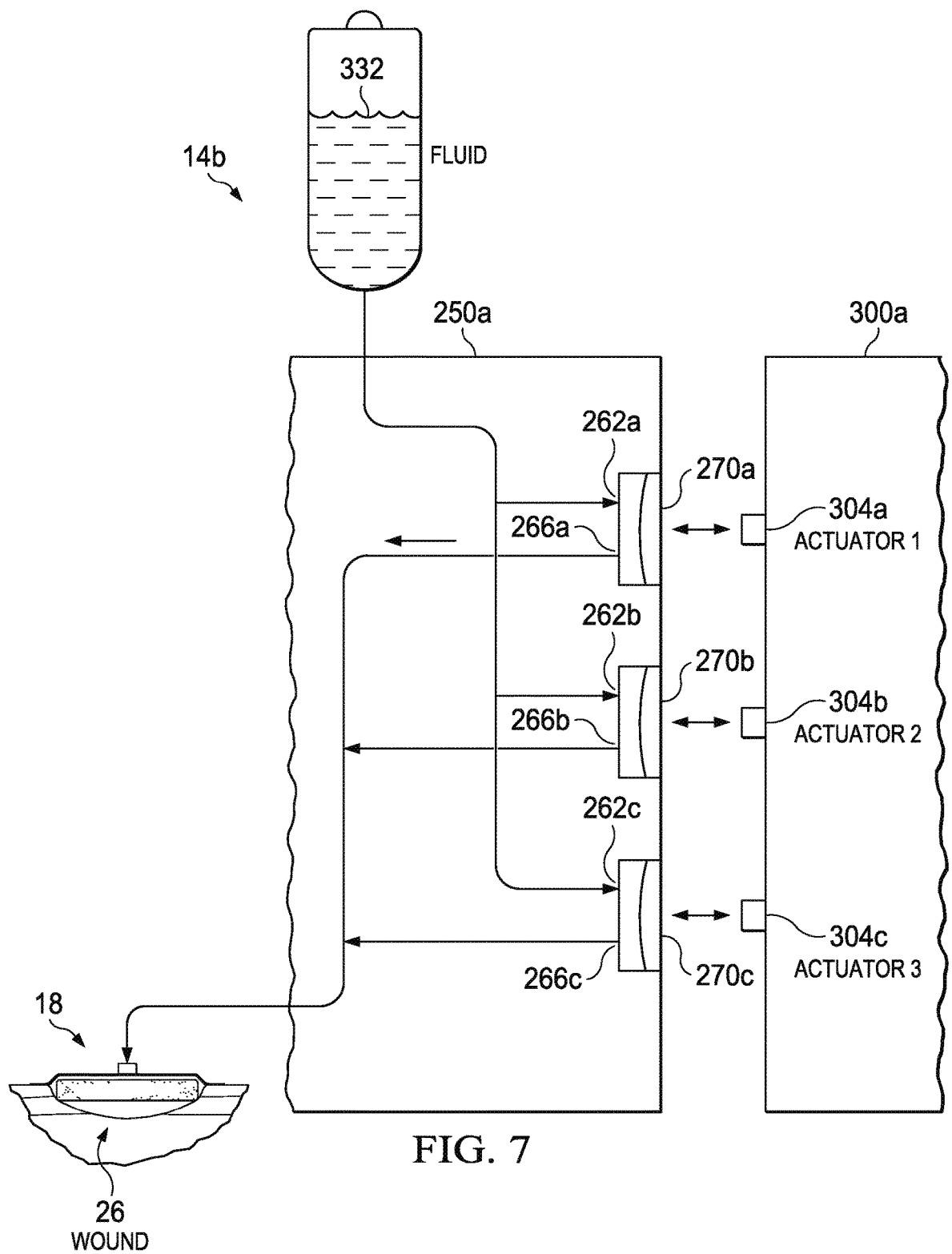
FIG. 7 depicts a side view of a portion of another embodiment of the present wound-treatment apparatuses.

FIG. 7 depicts a side view of a portion of another embodiment of the present wound-treatment apparatuses 14b. Apparatus 14b is similar in some respects to apparatus 14a. However, apparatus 14b comprises a housing 300a that is configured to be coupled to a plurality of pump cassettes (e.g., 250). In the embodiment shown, apparatus 14b also comprises: a plurality of actuators 304a, 304b, 304c coupled to housing 300a. In the embodiment shown, apparatus 14b is configured such that if one or more pump cassettes (e.g., 250) having a plurality of pump chambers (e.g., 254) and a plurality of diaphragms 270a, 270b, 270c configured to be movable to vary a volume in each of the plurality of pump chambers, the plurality of actuators 304a, 304b, 304c can be activated to move the diaphragms 270a, 270b, 270c. In the embodiment shown, the plurality of diaphragms 270a, 270b, 270c are coupled to a single pump cassette 250a (including a plurality of pump chambers). In other embodiments, a plurality of pump cassettes (e.g., 250) can be coupled to housing 300a.

In the embodiment shown, fluid container 332 is coupled in parallel to inlet valves 262a, 262b, 262c of each of the pump chambers, and outlet ports 266a, 266b, 266c are coupled in parallel to wound dressing 18. In some embodiments, apparatus 14b comprises a controller (not shown) coupled to actuators 304a, 304b, 304c and configured to activate the actuators. In some embodiments, the controller is configured to activate actuators 304a, 304b, 304c simultaneously. In some embodiments, the controller is configured to activate actuators 304a, 304b, 304c sequentially (e.g., 304a-304b-304c, 304a-304b-304c) such as, for example, to minimize fluctuations perceivable at wound dressing 18. Sequential activation can reduce pump ripple, and/or increase flow. In some embodiments, sequential activation can deliver very high flow-rates of fluid, and, by changing the selected actuators, deliver a very accurate final dose.

In some embodiments, apparatus 14b comprises: one or more automated readers (e.g., 312) configured to read an identifier (e.g., 316) of the one or more pump cassettes (e.g., 250, 250a) to determine the one or more properties of the one or more pump cassettes, and apparatus 14b is configured such that if one or more pump cassettes (e.g., 250, 250a) having an identifier (e.g., 312) are coupled to the housing, the one or more automated readers can read the identifier to determine the one or more properties. In some embodiments, apparatus 14b comprises a one or more pump cassettes (e.g., 250, 250a) having a plurality of pump chambers (e.g., 258) and a plurality of diaphragms (e.g., 270a, 270b, 270c) configured to be movable to vary a volume in each of the plurality of pump chambers. In some embodiments, the one or more pump cassettes are coupled to housing 300a. In the some embodiments, the plurality of diaphragms are the same size. In the embodiment shown, at least one of the plurality of diaphragms is a different size than at least one other of the plurality of diaphragms. For example, in the embodiment shown diaphragm 270c is larger than diaphragm 270b, and diaphragm 270b is larger than diaphragm 270a.

Figure 8:
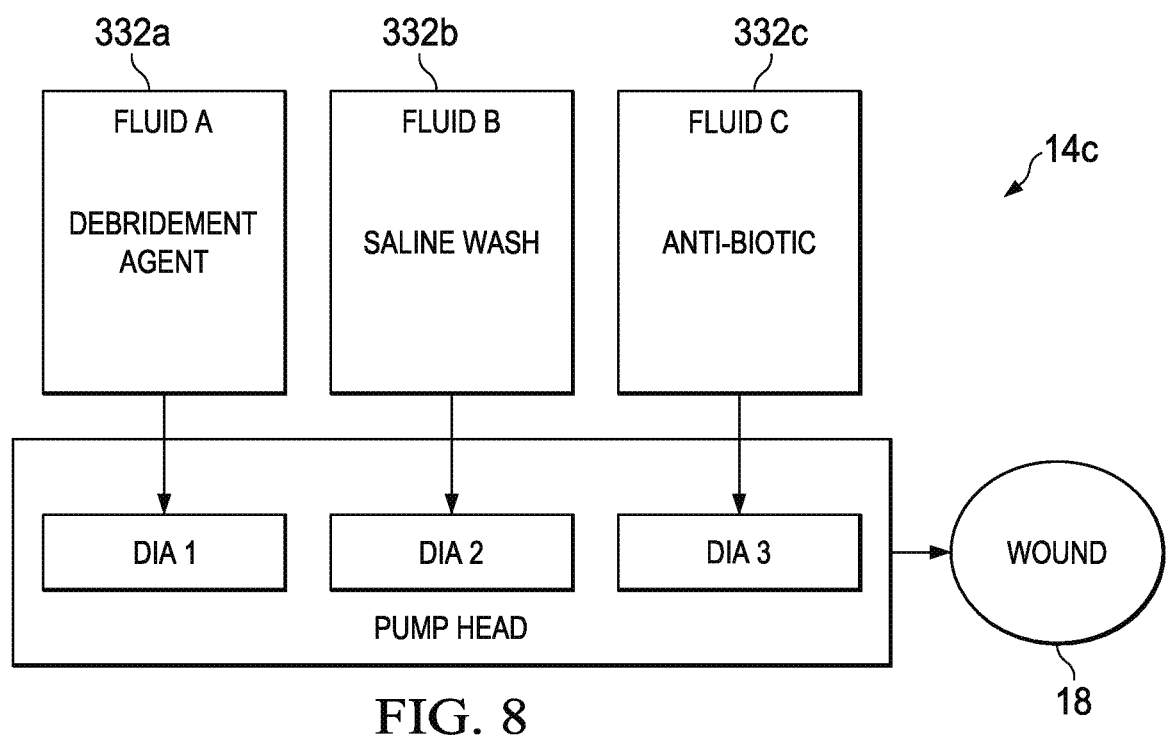
FIG. 8 depicts a diagram of a portion of another embodiment of the present wound-treatment apparatuses.

FIG. 8 depicts a diagram of a portion of another embodiment 14c of the present wound-treatment apparatuses. Apparatus 14c is similar in some respects to apparatus 14b. However, apparatus 14c is configured to be coupled to a plurality of fluid containers 332a, 332b, 332c, such that each of the plurality of pump chambers (and diaphragms) are configured to pump fluid from a different one of the plurality of fluid containers 332a, 332b, 332c. In this way, pump chambers and/or diaphragms of different sizes can pump different fluids in different amounts and/or at different rates. Apparatus 14c can be configured to deliver two or more fluids in combination, simultaneously or in sequence (e.g., to first flush a wound with saline which is then removed under NPWT, and then dose the wound with an antibiotic).

Some embodiments of the present methods comprise: coupling a wound dressing (e.g., 18) to a wound-treatment apparatus (e.g., 14a). In some embodiments, the wound-treatment apparatus comprises; a housing (e.g., 300) configured to be coupled to a pump cassette (e.g., 250); a vacuum source (e.g., 100) coupled to the housing and configured to be activated to apply negative pressure to a wound through the wound dressing; and an actuator (e.g., 304) coupled to the housing. Some embodiments of the present methods comprise: coupling a pump cassette (e.g., 250) to the housing of the wound treatment apparatus such that actuator can be activated to move the diaphragm (e.g., 270) and such that the outlet valve (e.g., 266) is in fluid communication with the wound dressing; and/or activating the actuator to move the diaphragm such that fluid is delivered to the wound dressing. In some embodiments, coupling a pump cassette is performed prior to coupling a wound dressing. Some embodiments comprise: activating the vacuum source such that negative pressure is applied to the wound dressing. Embodiments of the present wound-treatment methods can comprise embodiments of the present apparatuses (e.g., 14, 14a, 14b) and/or pump cassettes (e.g., 250, 250a).

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

It will be understood that the benefits and advantages described above may relate to one embodiment or may relate to several embodiments. It will further be understood that reference to 'an' item refers to one or more of those items, unless otherwise specified.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of this invention.

The invention claimed is:

1. A system for applying negative pressure and delivering fluids to a tissue site, comprising:
   a first pump having a first chamber closed by a first diaphragm movably operable to vary the volume of the first chamber, an inlet for receiving a first fluid, and an outlet for discharging the first fluid from the first chamber to the tissue site in response to movement of the first diaphragm;
   a first actuator adapted to be coupled to the first diaphragm and operable to move the first diaphragm to discharge a predetermined volume of the first fluid to the tissue site in a first predetermined fashion determined by a first code;
   a second pump having a second chamber closed by a second diaphragm movably operable to vary the volume of the second chamber, an inlet for receiving a second fluid, and an outlet for discharging the second fluid from the second chamber to the tissue site in response to movement of the second diaphragm;
   a second actuator adapted to be coupled to the second diaphragm and operable to move the second diaphragm to discharge a predetermined volume of the second fluid to the tissue site in a second predetermined fashion determined by a second code;
   wherein the first code relates to at least one property of the first diaphragm and the second code relates to at least one property of the second diaphragm; and
   a controller coupled to the first actuator and the second actuator and configured to receive the first code and the second code, and further configured to activate the first actuator and the second actuator to move the first diaphragm and the second diaphragm to discharge the first fluid and the second fluid based on the first and second codes.

2. The system of claim 1, wherein the at least one property related to first diaphragm and the second diaphragm includes one or more of the diameter of the diaphragm, the area of the diaphragm, the volume of the chamber, the stroke length of the diaphragm, and the change in volume in the chamber caused by the stroke length of the diaphragm.

3. The system of claim 1, wherein the controller is configured to actuate the first actuator and the second actuator simultaneously to deliver a mixture of the first fluid and the second fluid.

4. The system of claim 3, wherein the first fluid is an antibiotic solution and the second fluid is a saline solution for diluting the antibiotic solution.

5. The system of claim 1, wherein the controller is configured to actuate the first actuator and the second actuator sequentially to deliver the first fluid and the second fluid in sequence.

6. The system of claim 5, wherein the first fluid is a debridement agent and the second fluid is a saline solution.

7. The system of claim 1, wherein the first fluid and the second fluid are the same.

8. The system of claim 1, wherein the controller is configured to actuate the first actuator to deliver the first fluid to the tissue site, and then apply negative pressure to remove the first fluid from the tissue site.

9. The system of claim 1, wherein the controller is configured to apply negative pressure to flush the tissue site, and then to actuate the first actuator to discharge and deliver the first fluid to the tissue site.

10. The system of claim 1, further comprising one or more readers configured to read an identifier storing one or more of the first code and the second code, and wherein the controller is coupled to the reader for receiving the first code and the second code from the one or more readers.

11. The system of claim 10, wherein the first code and the second code relate to at least one property of the first diaphragm and the second diaphragm, respectively.

12. The system of claim 10, wherein the identifier comprises at least one of a radio-frequency identification (RFID) tag, a barcode, or a magnetic stripe.

13. The system of claim 10, wherein the actuator comprises a solenoid.

14. The system of claim 1, wherein at least one or more of the first code and the second code includes the identity of the first fluid and the second fluid.

15. The system of claim 1, wherein the inlet and the outlet each comprises at least one of a ball valve, a duckbill valve, or an umbrella valve.

16. The system of claim 1, wherein the diaphragm is operable to alternately increase and decrease the volume of the chamber.

17. The system of claim 1, wherein the inlet is open and the outlet is closed when the diaphragm is moved to increase the volume of the chamber.

18. The system of claim 1, further comprising a conduit having a first end coupled to the inlet and a second end configured to be coupled to a source of the first fluid and the second fluid.

19. The system of claim 18, wherein the fluid source is one or more fluid containers configured to be seated adjacent the pumps.

20. The system of claim 18, wherein the conduit has a predetermined length sufficiently long for coupling to one or more of the fluid containers.

* * * * *